United States Patent
Carrion et al.

(10) Patent No.: US 9,839,718 B1
(45) Date of Patent: Dec. 12, 2017

(54) INTRACORPORAL ULTRA HIGH PURITY CALCIUM SULFATE CAST MIXED WITH ANTIMICROBIALS FOR THE TREATMENT OF PENILE IMPLANT INFECTIONS

(71) Applicants: University of South Florida, Tampa, FL (US); United States Department of Veterans Affairs, Washington, DC (US)

(72) Inventors: Rafael Carrion, Tampa, FL (US); Daniel Roberto Martinez, Tampa, FL (US); Eihab Alhammali, Tampa, FL (US); Tariq Said Hakky, Riverview, FL (US)

(73) Assignees: University of South Florida, Tampa, FL (US); United States Department of Veterans Affairs, Washington, DC (US)

( * ) Notice: Subject to any disclaimer, the term of this patent is extended or adjusted under 35 U.S.C. 154(b) by 317 days.

(21) Appl. No.: 14/590,345

(22) Filed: Jan. 6, 2015

Related U.S. Application Data (60) Provisional application No. 61/926,041, filed on Jan. 10, 2014.

(51) Int. Cl.
*A61F 5/00* (2006.01)
*A61L 27/02* (2006.01)
(Continued)

(52) U.S. Cl.
CPC .............. *A61L 27/025* (2013.01); *A61F 2/26* (2013.01); *A61F 5/41* (2013.01);
(Continued)

(58) Field of Classification Search
CPC .................................. A61F 5/00; A61B 19/00
(Continued)

(56) References Cited

U.S. PATENT DOCUMENTS

| 5,147,403 A * | 9/1992 | Gitelis ...................... A61F 2/28 128/898 |
| 6,030,636 A | 2/2000 | Randolph et al. |
| 2013/0089593 A1 * | 4/2013 | Myntti ................... A01N 25/02 424/411 |

FOREIGN PATENT DOCUMENTS

DE 19620117 C1 7/1997

OTHER PUBLICATIONS

Ashley Parker et al, "Evaluation of Two Sources of Calcium Sulfate for a Local Drug Delivery System: A Pilot Study" published online May 7, 2011, pp. 1-9.*

(Continued)

*Primary Examiner* — Samuel Gilbert
(74) *Attorney, Agent, or Firm* — Michele L. Lawson; Nicholas R. Pfeifer; Smith & Hopen, P.A.

(57) ABSTRACT

The present invention includes a method for treating penile implant infections that uses a synthetic high-purity calcium sulfate mixed with antimicrobials, which is capable of providing prolonged exposure of antimicrobials to the infection site and capable of acting as an intracorporal filler preventing fibrosis and loss of phallic length. The technique is especially useful for high-risk patients, and provides another medium for which antimicrobial agents can be delivered to a surgical infection site while at the same time acting as a filler, preventing fibrosis, and loss of the space. The antimicrobial cast lasts 4-6 weeks, making timely re-implantation easier, and preventing intracorporal fibrosis and loss of phallic length.

14 Claims, 3 Drawing Sheets

(51) Int. Cl.
*A61F 5/41* (2006.01)
*A61F 2/26* (2006.01)

(52) U.S. Cl.
CPC ... *A61F 2005/411* (2013.01); *A61L 2300/406* (2013.01); *A61L 2400/06* (2013.01)

(58) Field of Classification Search
USPC .............................. 600/38–41; 128/897, 898
See application file for complete search history.

(56) References Cited

OTHER PUBLICATIONS

Stefanos Tsourvakas, "Local Antibiotic Therapy in the Treatment of Bone and Soft Tissue Infections", www.intechopen.com, Jan. 20, 2012, pp. 17-45.*

Laycock et al., A Simple Acoustic Technique to Assess the Setting Time of Antibiotic Loaded Calcium Sulphate, Presented at eCM XII: Implant Infection, Jun. 22-24, 2011, Congress Center, Davos, Switzerland.

John J. Mulcahy, Long-Term Experience With Salvage of Infected Penile Implants, The Journal of Urology, vol. 163, 481-482, Feb. 2000.

Niska et al., Vancomycin-Rifampin Combination Therapy Has Enhanced Efficacy against an Experimental *Staphylococcus aureus* Prosthetic Joint Infection, Antimicrobial Agents and Chemotherapy, Oct. 2013 vol. 57 No. 10, pp. 5080-5086.

Swords et al., A Preliminary Report on the Usage of an Intracorporal Antiobiotic Cast with Synthetic High Purity CaSO4 for the Treatment of Infected Penile Implant, J Sex Med; 10:1162-1169, Dec. 2013.

* cited by examiner

INTRACORPORAL ULTRA HIGH PURITY CALCIUM SULFATE CAST MIXED WITH ANTIMICROBIALS FOR THE TREATMENT OF PENILE IMPLANT INFECTIONS

CROSS-REFERENCE TO RELATED APPLICATIONS

This nonprovisional application is a continuation of and claims priority to provisional application No. 61/926,041, entitled "CARRION CAST: AN INTRACORPORAL ULTRA HIGH PURITY CALCIUM SULFATE CAST MIXED WITH ANTIMICROBIALS FOR THE TREATMENT OF PENILE IMPLANT INFECTIONS," filed Jan. 10, 2014 by the same inventors.

BACKGROUND OF THE INVENTION

1. Field of the Invention

This invention relates, generally, to surgical procedures. More specifically, it relates to the treatment of penile implant infections.

2. Brief Description of the Prior Art

Surgical infection has plagued prosthetic surgery since its inception. Despite great advances with penile prosthetic implants, more sophisticated antimicrobial regimens, and improvements in sterile technique; infections are still a major hurdle encountered by all urologists. Infection rates for virgin cases are 1-3%, increasing to 13.3% in revision, non-infected cases [1]. It has been reported up to 21.7% if simultaneous reconstruction occurs [2].

A number of culprit bacterial species have been implicated in penile prosthetic infections including, but not limited to *Staphylococcus epidermidis, Escherichia coli, Proteus mirabilis, Pseudomonas aeruginosa, Serratia marcescens*, and resistant species such as methicillin-resistant *Staphylococcus aureus*. The most common source of infection is skin flora, with introduction of these microorganisms at the time of surgery [3].

Once exposed to the implant, biofilm forms, a matrix that provides protection from antibiotic penetration and a nutrient-rich environment for survival. These bacteria remain dormant until they become planktonic (free-floating). At that time, symptoms associated with an active infection are manifested. This also represents the moment that antibiotics are effective against these microorganisms [4].

Infections are either clinical or subclinical. Virulent species of bacteria usually cause clinically apparent infections. These are more acute and easier to diagnose because of their flamboyant presentation, including fever, drainage, erythema, and erosion. Subclinical infections are more common, but more challenging to diagnose. Their presentation is subtle, and may sometimes include only pain [5].

Infection of penile implants poses a very difficult and complex hurdle that must be dealt with using innovative and creative modalities. Prevention of infection is of utmost importance, and a number of preoperative and intraoperative surgical plans have been developed. Different prepping agents and techniques, preoperative antibiotic regimens, intraoperative surgical site and implant soaking of antimicrobials, and antibiotic impregnated implants have all been used to prevent infection. Also, critically important, is limiting surgical time, since rate of infection is directly related to length of operating room time.

If an infection does occur, it must be dealt with in a timely fashion. If grossly infected, antibiotics alone are not sufficient and explantation is a necessity. The most conservative form of treatment includes removal of the infected implant with culture and irrigation of the space. Drains can be placed for a short period of time and routine antibiotic irrigation of the intracorporal (also referred to as corporal) spaces can be performed for a few days.

This approach causes corporal fibrosis, loss of phallic length, and possible development of morphologic deformity that ensues as healing takes place. This has led to the formation of salvage protocols, where the infection site is vigorously washed with a combination of antimicrobials and an immediate replacement of a new implant, usually in the form of semi-rigid rods. This acts as a spacer and prevents the aforementioned complications [6].

Not all patients are candidates for a salvage procedure. To name a few, it is not advised that those with cylinder extrusion, diabetics, and those with recurrent infections proceed with immediate salvage re-implantation. This subset of patients is likely to have an increase in morbidity. They are the most difficult to manage, and require aggressive rehabilitation postoperatively in order to prevent corporal fibrosis and loss of phallic length.

In the last ten years, with the advent of the antibiotic-coated inflatable penile prosthesis, infection rates have effectively decreased by 50% in virgin cases. This rate has been reported to be 1% (down from 2%). In revision cases, with combined washout and complete component exchange, studies have demonstrated infection rates of 2% (down from 10%) with the use of antibiotic-coated inflatable penile prosthesis [7].

These infection retardant coated implants have however, also lowered the percentage of coagulase-negative *Staphylococcus* infections, making way for more virulent species of bacteria, earlier onset of symptoms, and more toxic appearing patients when they do occur. These virulent species tend not to be as amenable to immediate salvage procedures.

Coagulase-negative *Staphylococcus* infections, mainly *Staphylococcus epidermidis* and *Staphylococcus lugdunesis*, usually present with an indolent, subclinical, local infection that typically manifests itself 2 to 3 months post-implantation, but may present years later. They are ideal for immediate salvage therapy [7].

Contrary to this, infections involving nonnosocomial bacteria (i.e., *Enterococcus, Pseudomonas aeruginosa, Escherichia coli*) tend to have a more clinically virulent presentation, with systemic symptoms. These patients tend to be sicker with fevers, chills, purulent drainage, and a more acute onset when compared to the timing of presentation for coagulase-negative *Staphylococcus* infections [7].

Although the rate of penile implant infections has decreased with antibiotic-coated implants, the change in the bacterial culprit to a more virulent species makes revision surgery more risky since patients tend to be more toxic. This subset of patients may require the utilization of innovative techniques for their management.

Therefore, there is a need for a new and improved approach in treating penile implant infection, especially in high-risk patients who are not candidates for immediate salvage replacement. Accordingly, what is needed is a method for treating penile implant infections that provides prolonged exposure of antimicrobials to the infection site, and is capable of acting as an intracorporal filler preventing fibrosis and loss of phallic length. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a method for treating penile implant infections that provides prolonged exposure of antimicrobials to the infection site, and is capable of acting as an intracorporal filler preventing fibrosis and loss of phallic length is now met by a new, useful, and nonobvious invention.

The novel method includes treating penile implant infections through a series of steps including removing of infected components from a patient's penis, injecting temporary synthetic high purity calcium sulfate into the patient's penis, allowing for a predetermined amount of treatment time to pass, and implanting a penile implant.

The novel method may also include the step of mixing the calcium sulfate with an antibiotic before injection. In a certain embodiment, the mixture of the calcium sulfate and the antibiotic has a chemical formula of SHPCaSO4A. The calcium sulfate preferably has a paste-like consistency during the injection and so the method may also include a step of molding the injected calcium sulfate in the patient's penis as the calcium sulfate begins to harden.

In a certain embodiment, the method includes a step of irrigating a surgical site before injecting the calcium sulfate. In yet another embodiment, the method includes a step of holding the glans of the patient's penis in a stretched position, from the moment the calcium sulfate is being injected until calcium sulfate solidifies.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention includes a method for treating penile implant infections using a novel temporary intracorporal antibiotic cast made of synthetic high purity calcium sulfate (SHPCaSO4) that acts as a "spacer" at the time of removal of an infected prosthesis while providing constant delivery of local antibiotic elution to the infected area. The benefit of using this antibiotic corporal spacer is continuous exposure to antibiotic/antifungal medication for the time that it takes to reabsorb (30-60 days). During that period, as the patient heals, the presence of this spacer prevents intracorporal fibrosis from ensuing, making subsequent re-implantation easier. This will also prevent loss of phallic length.

Calcium sulfate has commonly been used in orthopedic cases, mostly in a non-absorbable form, for the past century. In the orthopedic realm, this product is used as bone void filler for situations involving osteomyelitis in addition to trauma cases, where contamination and bone injuries usually go hand-in-hand. Its antimicrobial properties allow for continuous exposure of the area with the antibiotic and antifungal agents mixed into the calcium sulfate. Over time, it dissolves allowing new bone formation to take place, acting as a scaffold. Calcium sulfate's safety profile has been proven repeatedly and it does not appear to be absorbed systemically. Now with high-purity formulations, local reactions have not been reported. To this date, there are no reports of its application in the urologic literature, until now.

In addition to providing continuous local exposure of the antimicrobials and acting as filler, preventing fibrosis and loss of phallic length, the present invention includes the benefit of being feasible via penoscrotal corporotomies, as in both of the presented cases. Moreover, the operation can easily be performed via an infrapubic approach as well due to the ease of injecting the paste to fill the corporal bodies entirely. Once the corpora are closed, the cast will mold to take the shape of the space and appear as if a semi-rigid penile implant is present.

Example of the Present Invention

Figure 1:
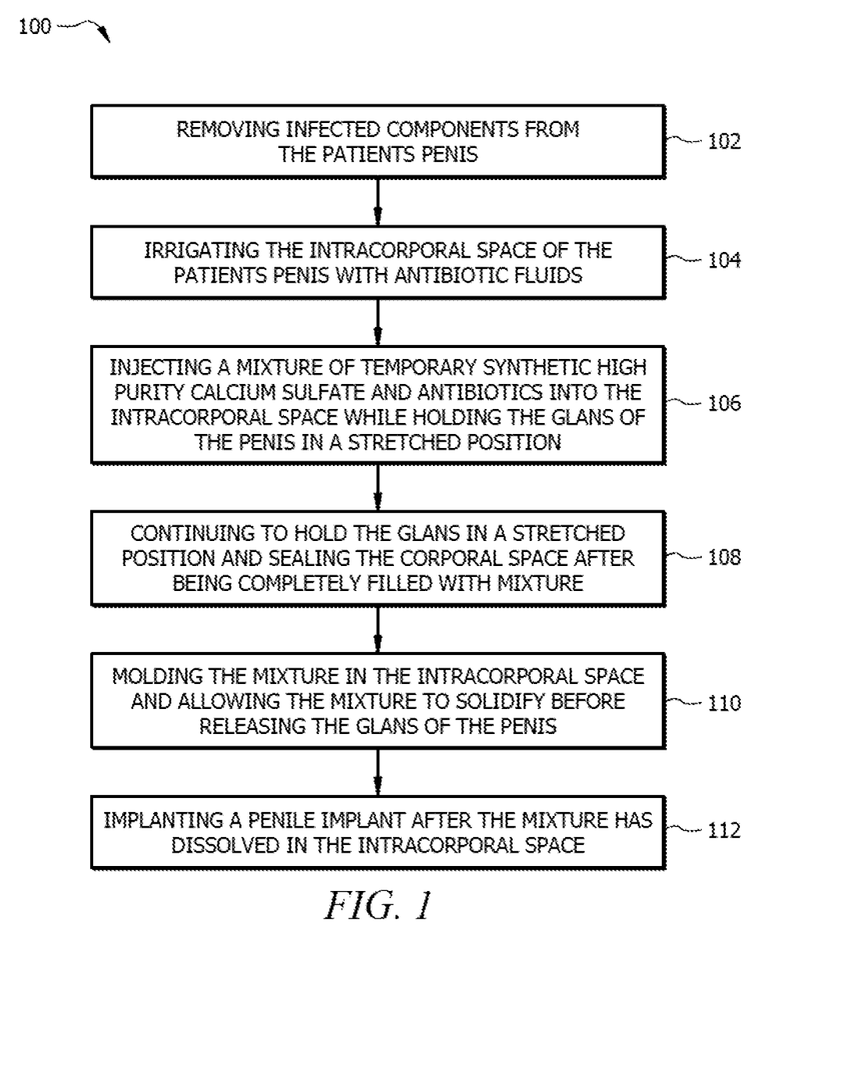
FIG. 1 provides a flowchart of a certain embodiment of the present invention.

A certain embodiment of the present invention, generally denoted by reference numeral 100, is provided in FIG. 1.

The method of treating penile implant infections as shown in FIG. 1 includes removing infected components from the patient's penis corporal space 102. The corporal space is then irrigated with antibiotic fluids 104. Once flushed, a mixture of temporary synthetic high purity calcium sulfate and antibiotics are injected into the corporal space while holding the glans in a stretched position 106. The glans are continually held in a stretched position until the mixture has solidified. The corporal space is sealed after the corporal space is completely filled with mixture 108. The mixture is then molded and allowed to solidify 110. Finally, a penile implant is implanted after the mixture has dissolved in the corporal space 112.

Experimental Approach

Two cases of patients with infection of their penile prosthesis were treated with placement of an intracorporal filler using an antibiotic cast of synthetic high purity CaSO4. Both had a complicated history of multiple penile implant surgeries, and were felt not to be candidates for immediate salvage re-implantation due to their complex history in addition to other factors that placed them at risk for reinfection (i.e., diabetes mellitus, obesity).

Patient A was a 48-year-old male with severe organic erectile dysfunction presented for removal of his infected penile implant (semi-rigid rods), and possible salvage, after noticing a skin tear on the right side of his phallus a few days prior, just proximal to the glans, and subsequent purulent drainage. He reported development of the subglandular lateral right tear, approximately a half of a centimeter in diameter, during coitus with his fiancé. He was eventually presented to the emergency room after the implant material became visible from the skin-hole. He received the semi-rigid penile implant on December 2011 after developing severe organic erectile dysfunction refractory to medical therapy. He had a history of coronary artery disease requiring angioplasty in 2010, cerebrovascular accident in 2003 with residual vascular dementia and cerebral atrophy, hypertension, and diabetes mellitus. He opted for a semi-rigid penile implant placed via a subglandular approach at an outside facility. He had reported worsening penile pain since the surgery, but had been able to perform coitus regularly with his partner. After developing the skin tear and purulent drainage with exposed implant, he was presented for treatment at our facility through the emergency room. In the operating room, a right, lateral, subglandular incision was made, and the sinus tract was excised. The right semi-rigid penile implant rod was removed, and the right corporal space was washed vigorously with a rifampin-bacitracin solution. The septum appeared intact; hence, the left rod was left in place. Tobramycin and vancomycin were mixed with the synthetic high purity CaSO4, creating a paste, which was then injected using a 12 cc syringe and 14F angiocatheter into the corporal space, filling the space completely, followed by immediate closure of the right sided corporotomy to prevent seepage of material. Once the paste began to harden, the cast was molded in a way to fill the corporal space, with an attempt to mirror the shape and length of the left rod. After this, the Dartos and skin layers were closed in standard fashion.

Patient B was a 53-year-old male who was presented for revision of his penile implant (semi-rigid rods) secondary to pain. There was no evidence of crossover, impending erosion, edema, erythema, induration, or purulence. He was able to use the implant for gentle coitus, with substantial amounts of lubrication. The implant was placed approximately 3 months prior. He had a history of multiple penile surgeries. In late 2010, he underwent excision of a ventral Peyronie's plaque with an SIS patch graft, but developed a hematoma 6 weeks after the surgery as well as subsequent recurrence of his deformity. Prior to this, he reported fairly good erectile function, which worsened with the procedure and complication. The postoperative recurrence of the defect and development of erectile dysfunction were substantial enough to warrant placement of an inflatable penile prosthesis, which occurred in mid-2011. This became infected, and subsequent explantation with salvage re-implantation using semi-rigid rods ensued. He developed a distal right-to-left crossover of the cylinders, pushing the left tip laterally and bulging it outward, causing him tenderness at the site. Revision surgery with replacement of semi rigid rods occurred in early 2012. He healed well from this surgery, and was able to resume sexual activity. Unfortunately, he developed chronic discomfort, as stated earlier, and was subsequently scheduled for another revision surgery. During this most recent procedure, a penoscrotal approach was used through his old incision. A substantial amount of scar tissue was lysed in order to expose the corpora bilaterally. A right corporotomy was made, revealing purulence emanating from the incision. The right semi-rigid implant rod was explanted, and it was noted that the tunical septum was completely obliterated distal to the peno-scrotal junction, with exposure of the right rod. The left semi-rigid rod was removed through the same right-sided corporotomy, and the corpora were washed vigorously with a rifampin-bacitracin solution. The defect left behind was in the shape of an inverted Y, with the proximal portion of the corpora having an intact septum, and the distal corpora fused, with the area of transition starting at the peno-scrotal junction. Tobramycin, vancomycin, and fluconazole (because of a previous history of fungal infection) were mixed with the synthetic high purity CaSO4, creating a paste, which was then injected using a 12 cc syringe and 14F angiocatheter into the corporal spaces, followed by immediate closure of the right sided corporotomy to prevent seepage of material. Once the paste began to harden, the cast was molded in a way to fill the corporal space as if semi-rigid rods were used to maintain the penis in a semi-erect state. After this, the Dartos and the skin layers were closed in standard fashion.

Preparation and Application

Currently, the only commercially available synthetic high purity calcium sulfate comes in the STIMULAN® Kit synthesized by Biocomposites Ltd. STIMULAN® is FDA-approved for cases where infections are either present or anticipated. It creates a unique crystal lattice structure with a consistent physiologic pH of 7.4 and high biocompatibility that can be mixed with most powder and liquid based antibiotic and antifungal agents. STIMULAN® resorbs in 30-60 days, preventing bacterial biofilm formation [8].

STIMULAN® can be manufactured in two kits, a "Rapid Cure Pack" and a "Standard Cure Pack", in 5, 10, and 20 cc (available only in the "Rapid Cure Pack") sizes. Both include CaSO4, pre-measured mixing solution bulbs, customizable pellet molds, and spatula. The "Rapid Cure Pack" also includes a mixing bowl and scraper, while the "Standard Cure Pack" provides a syringe and 8 cm extension tube. These allow for different methods of delivering and shaping the product. Commonly used in the pellet shape for orthopedic surgery, it may also be delivered as an injectable setting paste.

Figure 2:
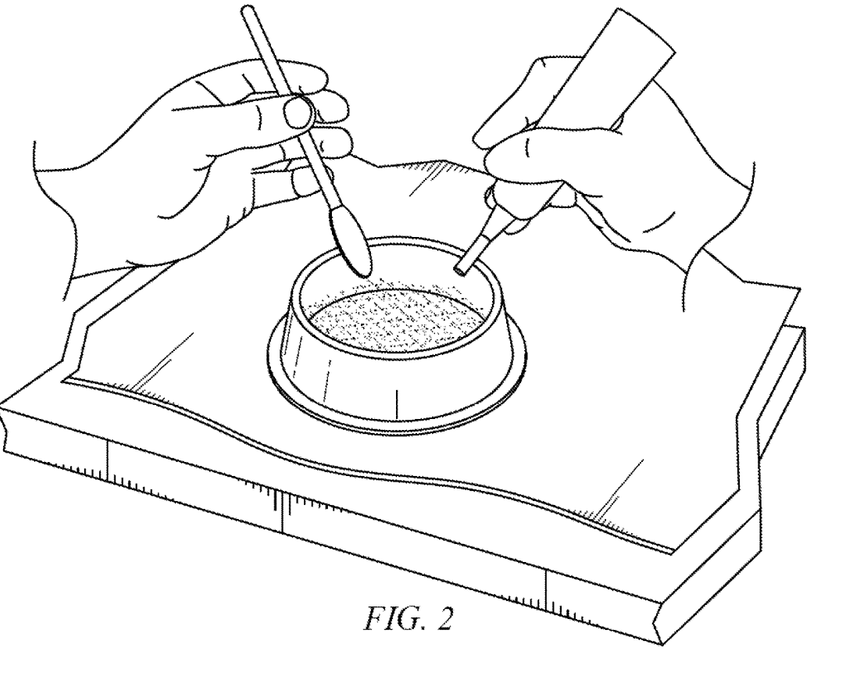
FIG. 2 depicts mixing of water to make paste. Performed after CaSO4 and antibiotic powder have been mixed. The spatula is used to mix, followed by the transfer of paste into a 12 cc syringe.
Figure 3:
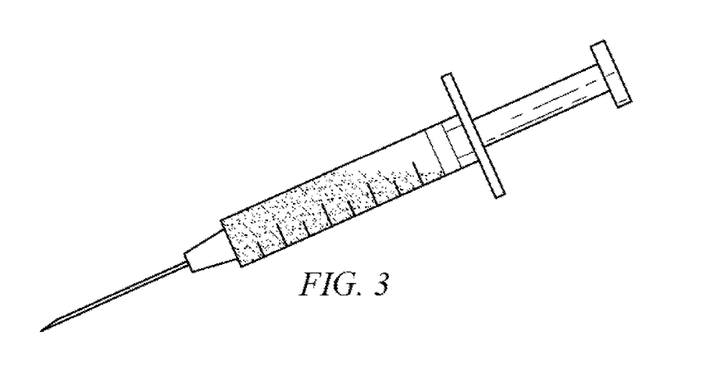
FIG. 3 depicts a syringe with paste of synthetic high-purity calcium sulfate mixed with antimicrobials.
Figure 4:
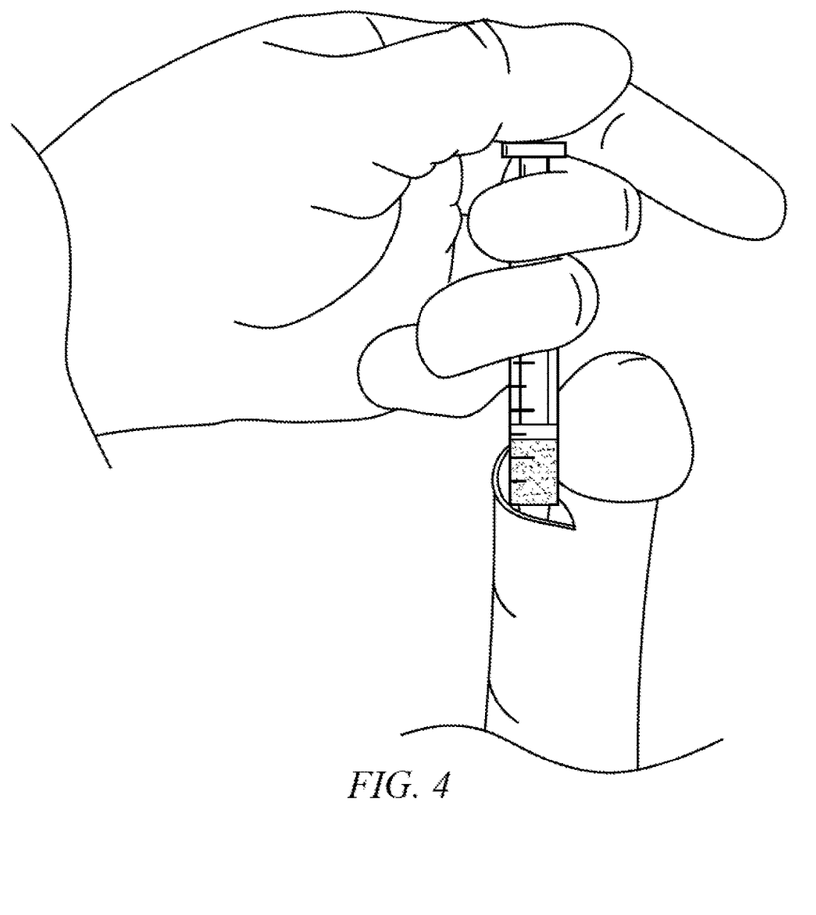
FIG. 4 depicts injection of paste into intracorporal space.

Once the CaSO4 is placed inside the packaged mixing bowl, the antibiotic is added, followed by the pre-measured mixing solution bulb. This is then mixed and, using the spatula provided in the package, is placed into a 12 cc syringe. Once the syringe is filled with the injectable paste, a 14F angiocatheter is used to inject the paste into the intracorporal space (FIGS. 2-4). The mixture will eventually solidify, but the set time depends on which antimicrobial agent is used. In the experimental case above, it took 5 minutes. Approximate set times can be reviewed in the STIMULAN® Kit pamphlet distributed by Biocomposites Ltd [8].

If the antibiotic is already in liquid form, the kit water does not need to be added to the mixture. If a powdered form of the antibiotic is used, then the kit water is added last prior to mixing with the spatula. The recommended mixing time is 60 seconds and 6 cc of water is recommended per antibiotic dose in order to provide a 10 cc volume of paste.

Experimental Results

Patient A denied pain postoperatively, and was discharged from the hospital on the day following his surgery. He remained on a 7-day course of trimethoprim-sulfamethoxazole, as is routine at the institution. His intra-operative culture grew gram-positive bacteria, but never speciated.

At his 2-week clinic visit, his incision had healed and the CaSO4 cast was still in place, resembling a right malleable rod on palpation. The left malleable rod that had been left due to it being isolated from the infection, and continued to be in good position. Patient A denied any discomfort.

At his 4-week postoperative visit, the cast had begun resorbing as was evident in its lack of integrity on palpation; there was still some cast material that could be felt, but only a small amount. However, there was no evidence of scarring that could be palpated throughout the right corpora on physical exam. Patient A was subsequently scheduled for re-implantation to occur at the 6-week postoperative mark.

During the surgery, a peno-scrotal approach was used. Once the right corporotomy was made, a gush of blood was encountered, similar to what is seen in virgin cases. A small amount of the cast was left behind that washed out easily with irrigation. There was no evidence of scarring of the intracorporal space. The left malleable implant was also removed, the spaces irrigated vigorously with antibiotic solution and a new three-piece inflatable implant was inserted with the rest of the case proceeding in standard fashion. Routine postoperative care was provided, and on most recent follow-up (6 months), patient A has not had a recurrence of infection, is sexually active, and content with his current situation.

Patient B remained comfortable postoperatively and did well clinically. He was discharged from the hospital the day after his explantation on trimethoprim-sulfamethoxazole and fluconazole. His intra-operative culture grew out *Candida albicans*.

On his 2-week postoperative visit, he denied pain, the peno-scrotal incision had healed, and the CaSO4 cast was in good position, again appearing as though a malleable penile prosthesis was in place. The patient did not return to his subsequent postoperative visits secondary to social reasons, and eventually, by week 12, he returned to clinic. It was evident that the cast had completely resorbed by this time, and a significant amount of scar tissue was palpable throughout the phallus of patient B on physical exam.

He was scheduled for re-implantation, occurring at postoperative week 15. Again, a peno-scrotal approach was utilized, and significant corporal fibrosis was encountered. Contrary to patient A, dilation of the space was difficult bilaterally, and only a right malleable implant could be placed. No evidence of residual CaSO4 cast was encountered during this salvage procedure. His postoperative course was uneventful, and on most recent follow-up (2 months), he reports being sexually active and content with his current situation. There has been no evidence of recurrent infection at this time.

As was evident in Patient A, after 4-6 weeks, the cast is resorbed, and replacement of an implant is made easier. Without evidence of fibrosis, minimal effort is required to dilate the space and place a new implant. There is also a hypothetical decrease in the risk of infection because of the extended course of antimicrobial exposure to the area, prior to re-implantation.

After 4-6 weeks, the cast had dissolved and a new implant was easily placed without evidence of fibrosis and loss of phallic length in patient A. Patient B had delayed salvage placement, and corporal fibrosis was encountered. This likely represents the importance of timely re-implantation prior to complete loss of the spacer. Regardless, both patients are content with surgical outcome, and at current follow up (mean 4 months), there has been no recurrence in infection. Both report being sexually active.

Example of Surgical Protocol

The surgical procedure can be completed through the following steps:

The first step typically includes initiating a standard preoperative antibiotic regimen. Followed by washing the surgical site preoperatively with two chlorohexidine soap scrubs (same used by the surgeon to scrub preoperatively), preferable for at least 5 minutes. At this point, two Chloroprep sticks should be obtained for prep and standard draping.

All infected implant components should be removed (recommend removing all components, including rear tip extenders and reservoirs). Immediately hand off infected implant materials to garbage and remove any tissue that is thought to be grossly infected. Then vigorously irrigate the surgical sites with a combination of Betadine, Bacitracin, Hydrogen Peroxide, Bactrim—smallest volume of irrigate. All should be mixed to fill separate blue basins, combined with normal saline and all should be delivered using a bulb syringe. It is recommend to start with betadine, followed by hydrogen peroxide, then bacitracin, and lastly Bactrim solution.

Using 2-0 Vicryl suture, preplace them in preparation for "water-tight" closure of the corporotomy or any other defect in the corpora. This prevents seepage of the STIMULAN slurry after initial injection into the corporal space, prior to solidification of the cast. Next, re-drape area with blue towels and pass off all tools used and exposed to infected implant material. Then cover surgical site with a blue towel and open STIMULAN "Rapid Cure Pack" +/−"Standard Cure Pack" 30 cc per corporal body (Larger implants/corpora may require >30 cc per corpora). If "Standard Cure Pack" use syringe and extension tubing included in the package place CaSO4 (powder form, packaged in small bottle) inside the packaged mixing bowl.

Mix the appropriate antimicrobials (in powder form) in the following dosages found in Table 1 below:

TABLE 1

| | | | | | | |
|---|---|---|---|---|---|---|
| Ciprofloxacin | 500 mg | P | | 5 cc | 1 L | 51 mins |
| Clarithromycin | 200 mg | P | | 5 cc | 1 L + 15 | 15 mins |
| Gentamycin | 240 mg | L | 80 mg/2 ml | 5 cc | NONE | 6 mins |
| Cefepime | 250 mg | P | | 5 cc | 15 | 20 mins |
| Cefepime | 500 mg | P | | 5 cc | <1 L | 21 mins |
| Meropenam | 1000 mg | P | | 10 cc | 1 L + 15 | 20 mins |
| Rifampin | 400 mg | P | | 5 cc | 1 L | 10 mins |
| Tobramycin | 240 mg | L | 80 mg/2 ml | 5 cc | None | 18 mins |
| Vanco + Gentamycin + Ampho-B | 1000 mg (Vanc)/ 480 mg (Gent)/ 200 mg (Amph) | P (Vanc)/ L (Gent)/ P (Amph) | 80 mg/2 ml (Gent) | 10 cc | NONE | 10 mins |
| Vanco + Tobramycin + Ampho-B | 1000 (Vanc)/ 480 mg (Tobro)/ 200 (Amph) | P (Vanc)/ L (Tobro)/ P (Amph) | 80 mg/2 ml (Tobro) | 10 cc | NONE | 25 mins |
| Vancomycin | 500 mg | P | | 5 cc | 1 L | 9 mins |
| Vancomycin | 2000 mg | P | | 10 cc | 1 L + 15 | 7 mins |
| Vancomycin | 3000 mg | P | | 10 cc | 1 L + 15 + A | 7 mins |
| Vancomycin + Amikacin | 250 mg (Vanc)/ 500 mg (Ami) | P (Vanc)/ L (Ami) | 500 mg/2 ml (Ami) | 5 cc | 1 L | 44 mins |
| Vancomycin + Cefotaxime | 250 mg (Vanc)/ 250 mg (Cefo) | P/P | | 5 cc | 1 L | 9 mins |
| Vancomycin + Ciprofloxacin | 250 mg (Vanc)/ 30 mg (Cipro) | P (Vanc)/ L (Cipro) | 400 mg/40 ml (Cipro) | 5 cc | NONE | 8 mins |
| Vancomycin + Ciprofloxacin | 250 mg (Vanc)/ 250 mg (Cipro) | P/P | | 5 cc | 1 L | 43 mins |
| Vancomycin + Clarithromycin | 250 mg (Vanc)/ 200 mg (Clarith) | P/P | | 5 cc | 1 L + 15 | 8 mins |
| Vancomycin + Gentamycin | 250 mg (Vanc)/ 120 mg (Gent) | P (Vanc)/ L (Gent) | 80 mg/2 ml (Gent) | 5 cc | NONE | 8 mins |
| Vancomycin + Piperacillin/ Tazobactram | 1000 mg (Vanc)/ 3.375 GM (Piper) | P/P | | 10 cc | 1 L + 15 | 35 mins |
| Vancomycin + Rifampin | 250 mg (Vanc)/ 200 mg (Rif) | P/P | | 5 cc | 1 L | 8 mins |
| Vancomycin + Tobramycin | 250 mg (Vanc)/ 120 mg (Tobro) | P (Vanc)/ L (Tobro) | 80 mg/2 ml (Tobro) | 5 cc | NONE | 29 mins |
| Vancomycin + Tobramycin + Nafcillin | 500 mg (Vanc)/ 240 mg (Tobro)/ 500 mg (Naf) | P (Vanc)/ L (Tobro)/ P (Naf) | 80 mg/2 ml (Tobro) | 5 cc | NONE | 38 mins |

ANTI FUNGAL

| | | | | | | |
|---|---|---|---|---|---|---|
| Fluconazole | 400 mg | P | | 5 cc | 1 L | 8 mins |
| Vancomycin + Fluconazole | 250 mg (Vanc)/ 250 mg (Flu) | P | | 5 cc | 1 L | 7 mins |
| Amphoteracin-B | 200 mg | P | | 10 cc | 15 + B | 29 mins |
| Vancommycin + Amphoteracin-B | 1000 mg (Vanc)/ 250 mg (Amph) | P/P | | 5 cc | 1 L + 15 + C | 15 mins |
| Vancommycin + Amphoteracin-B + Clindamycin | 1000 mg (Vanc)/ 200 mg (Amph)/ 600 mg (Clind) | P/P | | 10 cc | 1 L + 15 + D | 6 mins |
| Vancommycin + Amphoteracin-B | 1000 mg (Vanc)/ 200 mg (Amph) | P/P | | 10 cc | 1 L + 15 | 5 mins |

DID NOT SET (DNS)

| | | | | | | |
|---|---|---|---|---|---|---|
| Ceftriaxone | 500 mg | P/P | N/A | 5 cc | 2.0 ml | DNS |
| Bactrim (TMP/ SMZ) | 96 mg/480 mg | L | 16 mg/80 mg- 30 ml | 5 cc | NONE | DNS |
| Vancomycin + Bactrim | | | | 5 cc | NONE | DNS |
| Vancomycin + Ceftriaxone | 250 mg (V) + 250 mg (C) | P/P | N/A | 5 cc | 2.5 ml | DNS |
| Vancomycin + Tobra + Amph-B | | | | 10 cc | 2.5 ml | DNS |
| Vancomycin + Tobra + Clind | | | | 10 cc | 2.0 ml | DNS |
| Vancomycin + Tobramycin | | | | 10 cc | 2.0 ml | DNS |
| Cafazolin + Nafellin | | | | 5 cc | 2.0 ml | DNS |
| Nafellin | | | | 5 cc | 2.0 ml | DNS |
| Ertapenam | | | | 10 cc | 2.0 ml | DNS |

*Concentrations are for liquid antibiotics/antifungals only
A - Add 3.0 ml sterile water
B - Add 1.25 ml sterile water
C - Add 0.5 ml sterile water
D - Add 1.5 ml sterile water If the antibiotic is already in liquid form, the kit water does not need to be added to the mixture. If a powdered form of the antibiotic is used, then the kit water is added last prior to mixing with the spatula. USF Urology standard mixture is vancomycin 1 gram and tobramycin 1.2 grams in powdered form.

Next, add the pre-measured mixing solution bulb included in the "Rapid Cure Pack". The recommended mixing time is 60 seconds and 6 cc of water is recommended per antibiotic dose in order to provide a 10 cc volume of paste. Note: preparation is highly dependent on formation of water-saturated slurry. Once this consistency is reached, cease from further mixing and load into syringe or aspirate via catheter. In addition, stirring time is time-limited, as mixing progresses further in time. CaSO4 will harden or partially solidify making injection impractical. Of note, extra sterile water may be required if 2+ antimicrobial agents are used. It is recommend having a 12 cc syringe with sterile water ready in case extra volume is necessary, adding one drop at a time if necessary.

The ingredients are then mixed and, using the spatula provided in the package, the mixture is placed into a 12 cc syringe. The paste should be placed into the syringe by removing stopper and back loading it. Care should be taken to work quickly, since once the water is added the paste will harden into a cast in the time reported on Table 1.

Once the syringe is filled with the injectable paste, the stopper is replaced and a 14-16 gauge angiocatheter is used to inject the paste into the intracorporal space. If "Standard Cure Pack" is used, the extender will take the place of the angiocatheter. Immediately after filling the space with appropriate volume of STIMULAN, the preplaced Vicryl sutures should be tied and "water-tight" closure of the corpora should be achieved. An assistant should hold the glans in a stretched position, from the moment the paste is being injected until it eventually solidifies (set times depend on which antimicrobial agent is used and is reported in Table 1). The time for the paste to harden into a cast ranges from 2 minutes to 20 minutes, vancomycin and tobramycin, respectively.

Lastly close the surgical incision in multiple layers in order to prevent cast material from seeping out of the wound postoperatively. Patients should be informed that a small amount of seepage from the incision is normal, and that they should take precaution in order to prevent staining their clothes.

Glossary of Claim Terms

Paste-like Consistency: is a consistency having some amount of fluidity, such that it could pass through a syringe.

Penile Implant: is any implant received by the penis.

Treatment Time: is the time in which the calcium sulfate remains undisturbed in the patient's penis.

LIST OF REFERENCES

[1] Carson C C, Selph J P. Penile prosthesis infection: Approaches to prevention and treatment. Urol Clin N Am 2011; 38:227-35.

[2] Jarow J P. Risk factors for penile prosthesis infection. J Urol 1996; 156:402-4.

[3] Mulcahy J J. Long-term experience with salvage of infected penile implants. J Urol 2000; 183:481-2.

[4] Stewart P S, Costerton J W. Antibiotic resistance of bacteria in biofilms. Lancet 2001; 358:135-8.

[5] Selph J P, Carson C C. Penile prosthesis infection: Approaches to prevention and treatment. Urol Clin N Am 2011; 38:227-35.

[6] Maatman T J, Montague D K. Intracorporeal drainage after removal of infected penile prostheses. Urology 1984; 23:184-5.

[7] Wilson S K, Costerton J W. Biofilm and penile prosthesis infections in the era of coated implants: A review. J Sex Med 2012; 9:44-53.

[8] From the STIMULAN® Kit pamphlet distributed by Biocomposites Ltd. Staffordshire, UK.

[9] Wilson S K, Salem E A, Costerton W. Anti-infection dip suggestions for the Coloplast Titan Inflatable Penile Prosthesis in the era of the infection retardant coated implant. J Sex Med 2011; 8:2647-54.

[10] Martinez-Salamanca J I, Mueller A, Moncada I, Carballido J, Mulhall J P. Penile prosthesis surgery in patients with corporal fibrosis: A state of the art review. J Sex Med 2011; 8:1880-9.

[11] Dhabuwala C, Sheth S, Zamzow B. Infection rates of rifampin gentamicin-coated Titan Coloplast penile implants. Comparison with Inhibizone-impregnated AMS penile implants. J Sex Med 2011; 8:315-20.

Kelly Swords, M D, Daniel R. Martinez, M D, Jorge L. Lockhart, M D, and Rafael Carrion, M D. A Preliminary Report on the Usage of an Intracorporal Antibiotic Cast with Synthetic High Purity CaSO4 for the Treatment of Infected Penile Implant. J Sex Med 2013; 10:1162-1169.

Daniel R. Martinez, Eihab Alhammali, Tariq S. Hakky, Justin Emtage, Justin Parker, Rafael Carrion. The "Carrion Cast": Intracorporal Antimicrobial Cast Using Synthetic High Purity CaSO4 for the Treatment of Infected Penile Implant—Surgeon Protocol. (Attached)

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for treating penile implant infections, comprising:

removing of infected components from a patient's penis;

injecting temporary synthetic high purity calcium sulfate into the patient's penis; and holding a glans of the patient's penis in a stretched position, from a moment the calcium sulfate is being injected until the calcium sulfate solidifies.

2. The method of claim 1, further including the step of mixing the calcium sulfate with an antibiotic before injection.

3. The method of claim 1, further comprising a step of implanting a penile implant after a predetermined amount of treatment time.

4. The method of claim 1, wherein the calcium sulfate has a paste-like consistency during the step of injecting.

5. The method of claim 1, further comprising a step of molding the injected calcium sulfate in the patient's penis as the calcium sulfate begins to harden.

6. The method of claim 1, further comprising a step of irrigating an intracorporal space of the penis of the patient before injecting the calcium sulfate.

7. A method for treating penile implant infections, comprising:
   removing of infected components from a patient's penis;
   injecting temporary synthetic high purity calcium sulfate into the patient's penis;
   holding a glans of the patient's penis in a stretched position, from a moment the calcium sulfate is being injected until the calcium sulfate solidifies;
   allowing for a predetermined amount of treatment time to pass; and
   implanting a penile implant.

8. The method of claim 7, further comprising the step of mixing the calcium sulfate with an antibiotic before injection.

9. The method of claim 7, wherein the calcium sulfate has a paste-like consistency during the step of injecting.

10. The method of claim 7, further comprising a step of molding the injected calcium sulfate in the patient's penis as the calcium sulfate begins to harden.

11. The method of claim 7, further comprising a step of irrigating a corporal space of the penis of the patient before injecting the calcium sulfate.

12. A method for treating penile implant infections, comprising:
    removing of infected components from a patient's penis;
    injecting a mixture of temporary synthetic high purity calcium sulfate and antibiotics into a corporal space of the patient's penis;
    holding a glans of the patient's penis in a stretched position, from a moment the calcium sulfate is being injected until the calcium sulfate solidifies;
    sealing the corporal space of the patient's penis after the space has been completely filled;
    molding the mixture in the corporal space as the mixture begins to harden;
    allowing the injected mixture to dissolve inside the patient's penis; and
    implanting a penile implant.

13. The method of claim 12, wherein the mixture has a paste-like consistency during the step of injecting.

14. The method of claim 12, further comprising a step of irrigating the corporal space of the penis of the patient before injecting the mixture.

* * * * *